United States Patent
Hasegawa et al.

(10) Patent No.: US 6,228,324 B1
(45) Date of Patent: May 8, 2001

(54) STERILIZING METHOD FOR MEDICAL STERILIZATION PACKAGING AND INJECTION PACK

(75) Inventors: Mitsuru Hasegawa; Shuichi Maeda, both of Kitaibaraki; Tokushi Mitomi, Miura-gun; Takeshi Kanaguchi, Tokyo, all of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/197,614

(22) Filed: Nov. 23, 1998

(30) Foreign Application Priority Data

Nov. 28, 1997 (JP) .................................................. 9-343852
Dec. 26, 1997 (JP) .................................................. 9-367652

(51) Int. Cl.⁷ ........................................................ A61L 9/00
(52) U.S. Cl. ................................ 422/30; 206/364; 422/1; 422/28; 422/32; 422/33; 604/199
(58) Field of Search .................................. 422/1, 28, 30, 422/32, 33; 604/187, 191, 199, 246; 206/364

(56) References Cited

U.S. PATENT DOCUMENTS

| | | | |
|---|---|---|---|
| 4,230,663 | * 10/1980 | Forstrom et al. | 422/33 |
| 4,878,903 | * 11/1989 | Mueller | 604/199 |
| 5,407,070 | * 4/1995 | Bascos et al. | 206/365 |
| 5,615,772 | * 4/1997 | Naganuma | 206/365 |
| 5,792,422 | * 8/1998 | Lin et al. | 422/31 |
| 5,817,065 | * 10/1998 | Dufresne et al. | 604/199 |

FOREIGN PATENT DOCUMENTS

| | | |
|---|---|---|
| 44 28 291 | 2/1996 | (DE) . |
| 0302 420 | 7/1988 | (EP) . |
| 0 505 579 1 | 10/1991 | (EP) . |
| 0 624 518 | 11/1994 | (EP) . |
| 2 127 692 | 9/1982 | (GB) . |

OTHER PUBLICATIONS

TYVEK® Catalog, No date available.
TYVEK® Sterile Package News, vol. 1, 1994.
TYVEK® Sterile Package News, vol. 4, 1995.
TYVEK® for Sterile Packaging, 1996.
TYVEK® English translation of Hydrogen peroxide gas sterilization and TYVEK® No date available.

* cited by examiner

*Primary Examiner*—Krisanne Thornton
(74) *Attorney, Agent, or Firm*—Dike, Bronstein, Roberts & Cushman, LLP; David G. Conlin

(57) ABSTRACT

The sterilizing method according to the present invention is a method of sterilizing a medical product by a hydrogen peroxide gas while keeping the packaged condition. In such a sterilizing method, a packaging container (1) capable of allowing the hydrogen peroxide gas to penetrate therethrough is used, and after completion of the sterilizing treatment, the packaging container (1) is subjected to degassing treatment while heating, thereby removing the hydrogen peroxide gas from the inside thereof. As a result, it is possible to conduct the treatment efficiently and surely prevent the hydrogen peroxide gas from remaining in the packaging container. In addition, the injection packs (P) according to the present invention comprises the packaging container (1) and a medicine-filled injector (4) enclosed in the packaging container. In the injection packs (P), a container body (2) has such a specific shape which can ensure a sufficient gas-penetrating area of a sterile paper by which the container body is sealed, when the injection pack are stacked up in multiple stages. Accordingly, upon the treatment, it becomes possible to penetrate the hydrogen peroxide gas into the packaging container (1) for a short period of time and degas the packaging container (1) for removing the hydrogen peroxide gas from the inside thereof.

15 Claims, 5 Drawing Sheets

STERILIZING METHOD FOR MEDICAL STERILIZATION PACKAGING AND INJECTION PACK

BACKGROUND OF THE INVENTION

The present invention relates to a sterilizing method for medical sterilization packaging and an injection pack. More particularly, the present invention relates to a method of sterilizing a medical product, e.g., a medicine-filled injector enclosed in a packaging container, by a hydrogen peroxide gas while keeping the packaged condition, which method is capable of efficiently conducting the sterilizing treatment and of surely preventing the hydrogen peroxide gas from remaining in the packaging container, and to an injection pack comprising a packaging container and a medicine-filled injector enclosed in the packaging container, which is sealed by a sterile paper and capable of mainly allowing only the sterilizing gas to penetrate therethrough, and enables the medicine-filled injector enclosed in the packaging container to be readily sterilized.

Medicine-filled injectors, have been suitably subjected to medical sterilization packaging and then distributed or marketed, as well as other disposable medical products or appliances. The medical sterilization packaging is a packaging method which comprises using a packaging container composed of a container body composed of a synthetic resin having a gas-barrier property, and a sterile paper as a lid which can allow a sterilizing gas to penetrate therethrough and can be welded to the container body, and after enclosing the medical product in the packaging container, exposing the medical product to a sterilizing gas while keeping the packaged condition, whereby an inside of the packaging container is sterilized by the sterilizing gas which is caused to penetrate thereinto through the sterile paper.

In the above-mentioned medical sterilization packaging, in order to solve the problem caused by toxicity of the sterilizing gas, it has been studied for sterilization of various medical products to use a hydrogen peroxide gas instead of ethylene oxide. However, even though any of ethylene oxide and the hydrogen peroxide gas is used, it has been inevitably required that the packaged medical products are subjected to post-treatment for removing the sterilizing gas from the inside of the packaging container, thereby eliminating an adverse influence on human bodies due to the residual harmful gas upon distribution thereof. Incidentally, the techniques concerning disinfection or sterilization using hydrogen peroxide has been described in Japanese Patent Publication (KOKOKU) No. 61-4543 (1986) (GB-A 2127692), Japanese Patent Application Laid-open (KOKAI) No. 1-121057 (1989) (EP-A 0302420) or the like. In addition, the techniques concerning medicine-filled injectors has been described in Japanese Patent Application Laid-open (KOKAI) No. 4-150868 (1992) (EP-A 0505579) or the like.

Meanwhile, in the medical sterilization packaging, in order to completely remove the sterilizing gas from the packaging container after the sterilizing treatment, it is necessary to allow the packaged medical products to stand for a considerably long period of time. The gas-removing operation has resulted in low productivity of the packaged medical products. Especially, in the case of the injection packs, since the injection packs are stacked up in multiple stages when sterilized, there arises a problem that the efficiency of penetrating the sterilizing gas through the sterile paper is deteriorated, because the surface of the sterile paper is disadvantageously covered by the container body of the upper or lower packaging container stacked. Further, in the injection packs, in view of a shape of the packaging container thereof, there has also been caused a problem that a degassing efficiency of removing the penetrated gas from an inside of the packaging container is deteriorated.

Furthermore, in the above-mentioned medical sterilization packaging, when a container composed of a polyester-based resin is used as the packaging container, the container has a high adsorptivity for the sterilizing gas, so that it becomes more difficult to remove the sterilizing gas therefrom. For this reason, there have been used many containers composed of vinyl chloride-based resins as a main component. As a result, the visibility of an inside of the container is deteriorated, and there has been further caused a problem that a chlorine gas or hydrogen chloride gas is generated upon disposal of the vinyl chloride-based resins.

SUMMARY OF THE INVENTION

The present invention has been attained in order to solve the above-mentioned problems.

It is an object of the present invention to provide a method of sterilizing a medical product, e.g., a medicine-filled injectors with a hydrogen peroxide gas while keeping the packaged condition for medical sterilization packaging, which method is capable of efficiently conducting the sterilizing treatment, can surely prevent the hydrogen peroxide gas from remaining in the packaging container, and is applicable to such a case where a packaging material composed of a polyester-based resin is used.

It is another object of the present invention to provide an injection pack comprising a suitably molded packaging container and a medicine-filled injector enclosed in the packaging container which is sealed by a sterile paper and capable of readily sterilizing the medicine-filled injector enclosed therein.

To accomplish the aims, in a first aspect of the present invention, there is provided a method of sterilizing a medical product enclosed in a packaging container by a hydrogen peroxide gas, comprising:

using as said packaging container, a container comprising a container body composed of a synthetic resin having a gas-barrier property, and a sterile paper capable of allowing said hydrogen peroxide gas to penetrate therethrough and weldable to said container body; and after the sterilization by said hydrogen peroxide gas, subjecting said packaging container enclosing said medical product to degassing treatment while heating, thereby removing said hydrogen peroxide gas from an inside of said packaging container.

In a second aspect of the present invention, there is provided an injection pack comprising a packaging container and a medicine-filled injector enclosed in said packaging container, said packaging container comprising a container body which is composed of a transparent resin, integrally molded into an approximate elongated vessel shape and opened at bottom thereof, and a sterile paper composed of a sheet material capable of allowing a sterilizing gas to penetrate therethrough and closing the open bottom of said container body, said container body comprising a first swelled portion for receiving a needle-fitting portion of an injector cylinder of said medicine-filled injector, a second swelled portion for receiving an approximately central portion of said medicine-filled injector, a third swelled portion for receiving a flange of said injector cylinder and a pusher of a piston rod, and two constricted portions connecting said swelled portions to each other, said third swelled portion being formed into a saddle shape recessed at a central portion thereof when viewed from the longitudinal side of said container body.

DETAILED DESCRIPTION OF THE INVENTION

Figure 1:
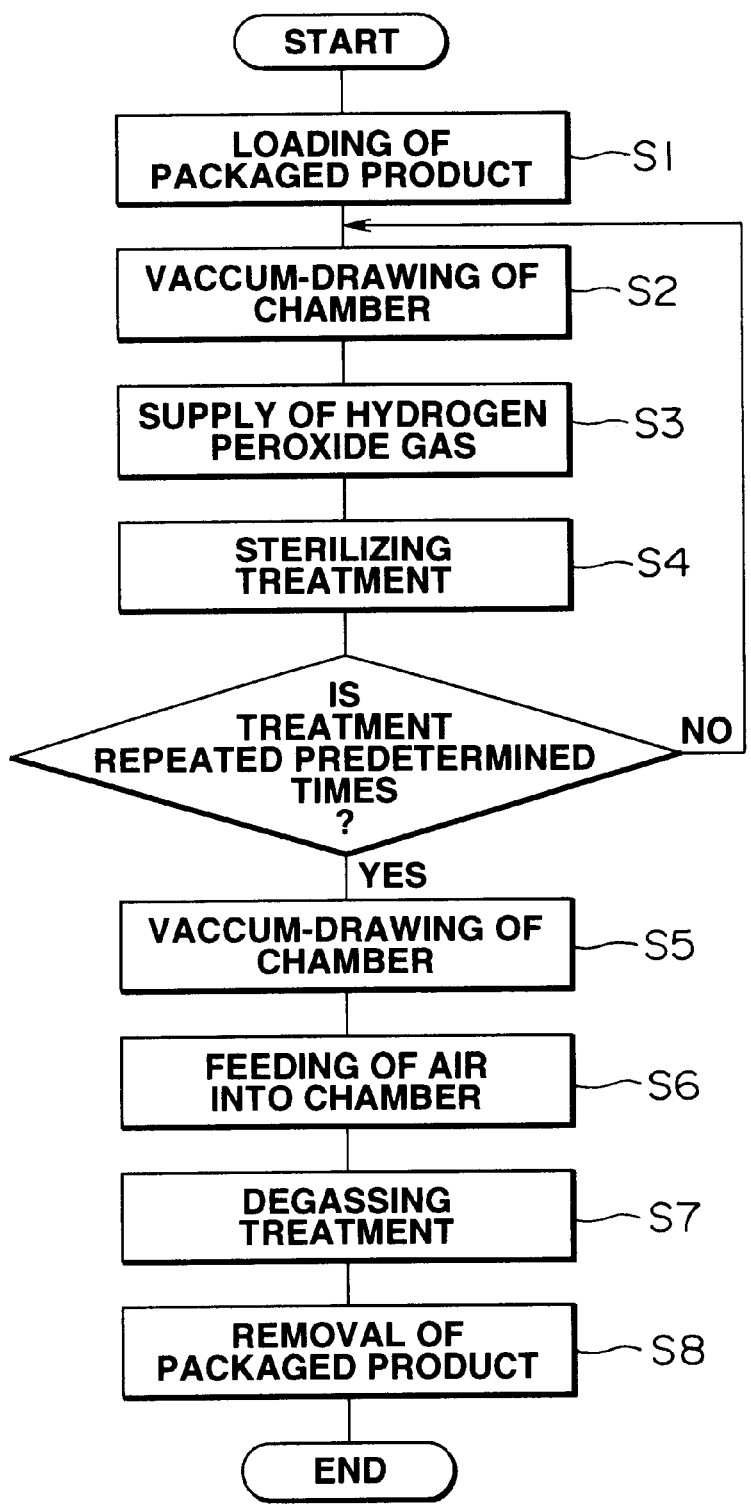
FIG. 1 is a flow chart showing respective steps in a sterilizing method according to the present invention.

The above objects of the present invention can be accomplished by specific embodiments of a sterilizing method for medical sterilization packaging and an injection pack as described in the following items (1) to (3).

(1) A sterilizing method of sterilizing a medical product enclosed in a packaging container by a hydrogen peroxide gas, which method comprises:

using as the packaging container, a container comprising a container body composed of a synthetic resin having a gas-barrier property and a sterile paper as a lid which is capable of allowing the hydrogen peroxide gas to penetrate therethrough and weldable to the container body; and after completion of the sterilizing treatment by the hydrogen peroxide gas, degas-treating the packaging container while heating, thereby removing the hydrogen peroxide gas from the inside thereof.

In the above sterilizing method, after sterilizing the packaged medical product by the hydrogen peroxide gas which is allowed to penetrate through the sterile paper of the packaging container, the packaged medical product is heated to promote the desorption of the hydrogen peroxide gas adsorbed into the container body, thereby removing the hydrogen peroxide gas remaining within the packaging container.

Further, in the above sterilizing method, the medical product enclosed in the packaging container is placed in a chamber as a sterilizer and then sterilized. Thereafter, while circulating heated air to the chamber, the hydrogen peroxide gas contained in the circulated air is decomposed by catalytic reaction, so that the concentration of the hydrogen peroxide gas in the chamber can be always maintained at a low level during the degassing treatment for removal of the hydrogen peroxide gas, thereby enabling the hydrogen peroxide gas to be removed efficiently and safely.

Furthermore, in the above-mentioned method, by repeating the operation of supplying the hydrogen peroxide gas to the chamber whose inside pressure is reduced, several times, it becomes possible to rapidly and surely penetrate the hydrogen peroxide gas into the packaging container in the sterilization treatment.

(2) An injection pack enclosing a medical product wherein the medical product is a medicine-filled injector and an inside of a packaging container comprising a container body whose open bottom is sealed by a sterile paper, is sterilized by a hydrogen peroxide while keeping the sealed condition.

(3) An injection pack comprising a packaging container and a medicine-filled injector enclosed in the packaging container wherein the packaging container comprises a container body which is composed of a transparent resin, integrally molded into an approximately elongated vessel shape and opened at bottom thereof, and a sterile paper which is composed of a sheet material capable of allowing a sterilizing gas to penetrate therethrough and by which the open bottom of the container body is sealed. The container body comprises a first swelled portion for receiving a needle-mounting portion of an injector cylinder of the medicine-filled injector, a second swelled portion for receiving an approximately central portion of the medicine-filled injector, a third swelled portion for receiving a flange of the injector cylinder and a pusher of a piston rod and two constricted portions connecting respective swelled portions to each other. The third swelled portion is formed into a saddle shape recessed at a central portion thereof, when viewed from a longitudinal side of the container body.

The above injection packs are stacked up in multiple stages when sterilized. Upon the sterilization, each constricted portion of the container body forms a gap between the upper and lower containers stacked, thereby allowing the sterilizing gas to pass through a whole part of the stacked-up injection packs. Since the third swelled portion for receiving the flange of the injector cylinder and the pusher of the piston rod which is the largest one among the three swelled portions, is formed into a saddle shape recessed at a central portion thereof, the contact area between the third swelled portion and the adjacent upper or lower packaging container becomes small, thereby enhancing an efficiency of contact between the sterile paper of the packaging container and the sterilizing gas.

In addition, in the above-constituted injection pack, it is preferred that the height of the second swelled portion is lower than those of the first and third swelled portions in order to further reduce a contact area between the container body and the sterile paper of the other packaging container when the injection packs are stacked up in multiple stages.

The sterilizing method according to the present invention is a sterilizing method for so-called medical sterilization packaging in which a medical product (including drugs, medical appliances or the like) enclosed in a specific packaging container is sterilized by a hydrogen peroxide gas while keeping the packaged condition. As a typical packaged medical product suitable for the medical sterilization packaging, there may be exemplified an injection pack comprising a packaging container and a medicine-filled injector enclosed in the packaging container. An injector is previously filled with a predetermined medicine and immediately usable by fitting a needle thereto as described in the above Japanese Patent Application Laid-open (KOKAI) No. 4-150868 (1992) (EP-A505579). The injection pack enclosing a medicine-filled injector is one specific form of the medical sterilization packaging in which an inside of the packaging container is sterilized by a sterilizing gas without heating. Further, the hydrogen peroxide gas used in the present invention can show a high germicidal action and a relatively low toxicity as compared to those of an ethylene oxide gas and is, therefore, a suitable sterilizing gas.

The preferred embodiments of the present invention are explained with reference to the accompanying drawings. In advance of the explanation of the above sterilizing method, there is described an injection pack to which the sterilizing method according to the present invention can be suitably applied. The injection pack designated by reference numeral (P) in FIGS. 3 and 4, comprises a packaging container (1) and a medicine-filled injector (4) enclosed in the packaging container. As is known in the art, the medicine-filled injector (4) is such an injector which can be immediately used by fitting a needle thereto, and comprises an injector cylinder (41) whose needle-mounting portion is fitted with a cap (42), a piston rod (44) having a piston at a tip end thereof and inserted into the injector cylinder (41), and a medicine filled in the injector cylinder (41). Examples of suitable medicines filled in the medicine-filled injector (4) may include those unsuitable for heating, typically, a sodium hyaluronate solution or the like.

Figure 3:
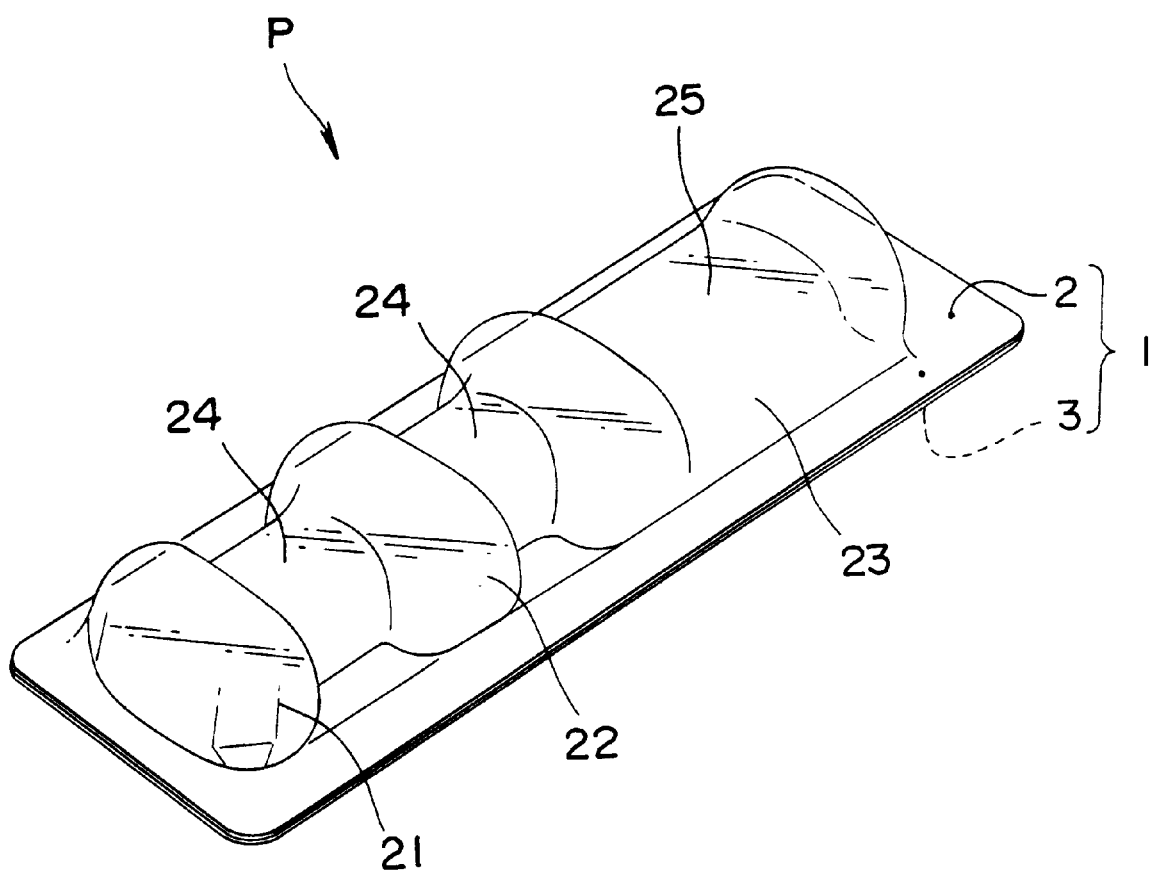
FIG. 3 is a perspective view showing an outer contour of a packaging container of an injection pack.

The packaging container (1) comprises a container body (2) composed of a synthetic resin having a gas-barrier property and a sterile paper (3) as a lid capable of allowing a hydrogen peroxide gas to penetrate therethrough and weldable to the container body (2). It is preferred that the container body has first to third swelled portions and two constricted portions connecting these swelled portions to each other. In the further preferable embodiment of the present invention, as shown in FIG. 3, the packaging container (1) comprises a container body (2) composed of a transparent resin, integrally molded into an approximately elongated vessel shape and opened at bottom, and a sterile paper (3) composed of a sheet material capable of allowing the sterilizing gas to penetrate therethrough and sealing the opened bottom of the packaging container (1). As resin materials for the container body (2), there may be used any appropriate thermoplastic resins capable of inhibiting bacteria from penetrating therethrough and visually observing contents therein. From the standpoint of the gas-barrier property and transparency, it is preferred that the container body (2) be composed of polyester-based resins such as polyethylene terephthalate (PET), polybutylene terephthalate (PBT) or the like.

More specifically, the container body (2) may be produced from a PET film having a thickness of 200 to 600 $\mu$m by a molding method such as a blister-molding method or a deep-drawing method. Especially, the container body (2) composed of the PET film is free from generation of harmful gases such as a chlorine gas upon disposal unlike vinyl chloride and is, therefore, a suitable packaging material from the standpoint of preventing environmental pollution.

As the sheet materials for the sterile paper (3), there may be suitably used those capable of inhibiting microorganism such as bacteria from penetrating therethrough but allowing gases such as a sterilizing gas and air to penetrate therethrough, e.g., a high-density polyethylene sheet material known as "TYVEK 1073B" (tradename, produced by Du Pont Inc.). Such a sterile paper (3) can be welded to the container body (2) by a ultrasonic welding method or a heat-welding method.

In the injection pack (P) of the present invention, the container body (2) comprises:

a first swelled portion (21) for receiving a tip end of an injector cylinder (41) of the medicine-filled injector (4), i.e., a needle-mounting portion fitted with a cap (42), a second swelled portion (22) for receiving an approximately central portion of a whole length of the medicine-filled injector (4) into which a piston rod (44) is inserted up to the mid position of full insertion, a third swelled portion (23) for receiving a flange (43) of the injector cylinder (41) and a pusher (45) (larger-diameter of end portion) of a piston rod (44), and two constricted portions (24), (24) connecting the respective swelled portions to each other.

That is, the first swelled portion (21) and the third swelled portion (23) of the container body (2) form relatively large spaces on both sides of the medicine-filled injector (4) and exhibit a function of temporarily storing the sterilizing gas diffused into delicate portions of the medicine-filled injector (4) such as clearances between the injector cylinder (41) and the piston rod (44). Further, the central second swelled portion (22) can function as a bending fulcrum of the container body (2), thereby enabling the medicine-filled injector (4) to be readily and hygienically taken out of the packaging container (1).

In addition, the respective constricted portions (24) of the container body (2) serve to define clearances between the upper and lower injection packs (P) when many injection packs (P) are stacked up in multiple stages in the below-mentioned sterilization treatment, thereby facilitating the flow of the sterilizing gas such as a hydrogen peroxide gas or air. Further, from this viewpoint, it is preferred that the first swelled portion (21) and the third swelled portion (23) of the container body (2) act as supporting points for stacking up the injection packs, and preferably, the height of the second swelled portion (22) is lower than those of the first swelled portion (21) and the third swelled portion (23).

Figure 5:
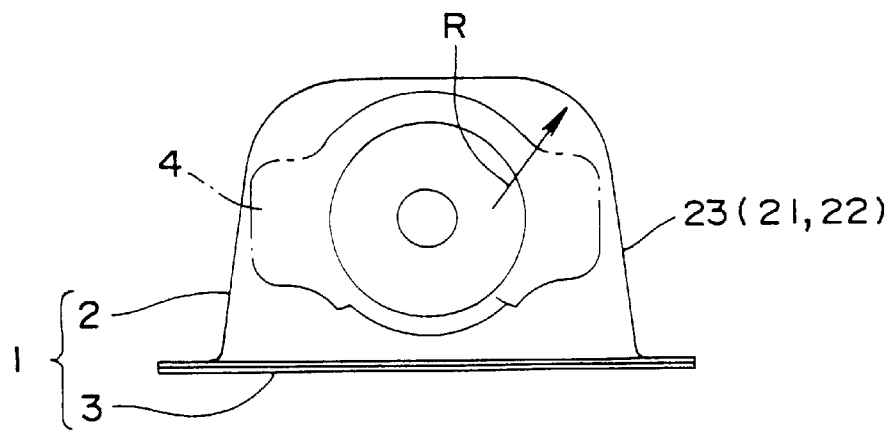
FIG. 5 is a sectional view showing shapes of swelled portions of the packaging container and taken in the direction perpendicular to the longitudinal direction of a container body thereof.

Furthermore, as shown in FIG. 5, corner portions of the first swelled portion (21), the second swelled portion (22) and the third swelled portion (23) have a radius of curvature (R) of 5 to 20 mm in order to facilitate the flow of the sterilizing gas or air and reduce the contact area between each swelled portion and the sterile paper (3) of the adjacent upper or lower injection pack (P) when the injection packs (P) are stacked up in multiple stages.

The feature of the container body (2) of the present invention lies in the specific shape of the third swelled portion (23). Namely, in order to ensure an effective gas-penetrating area of the sterile paper (3) upon the sterilization treatment of the injection pack (P), the third swelled portion (23) of the container body (2) is formed into a saddle shape recessed at a central portion thereof when viewed from the longitudinal side of the container body (2). More specifically, as shown in FIG. 3, the third swelled portion (23) is formed with protrusions at front and rear ends thereof when viewed along the longitudinal direction, and with a saddle portion (25) between the protrusions.

Figure 4:
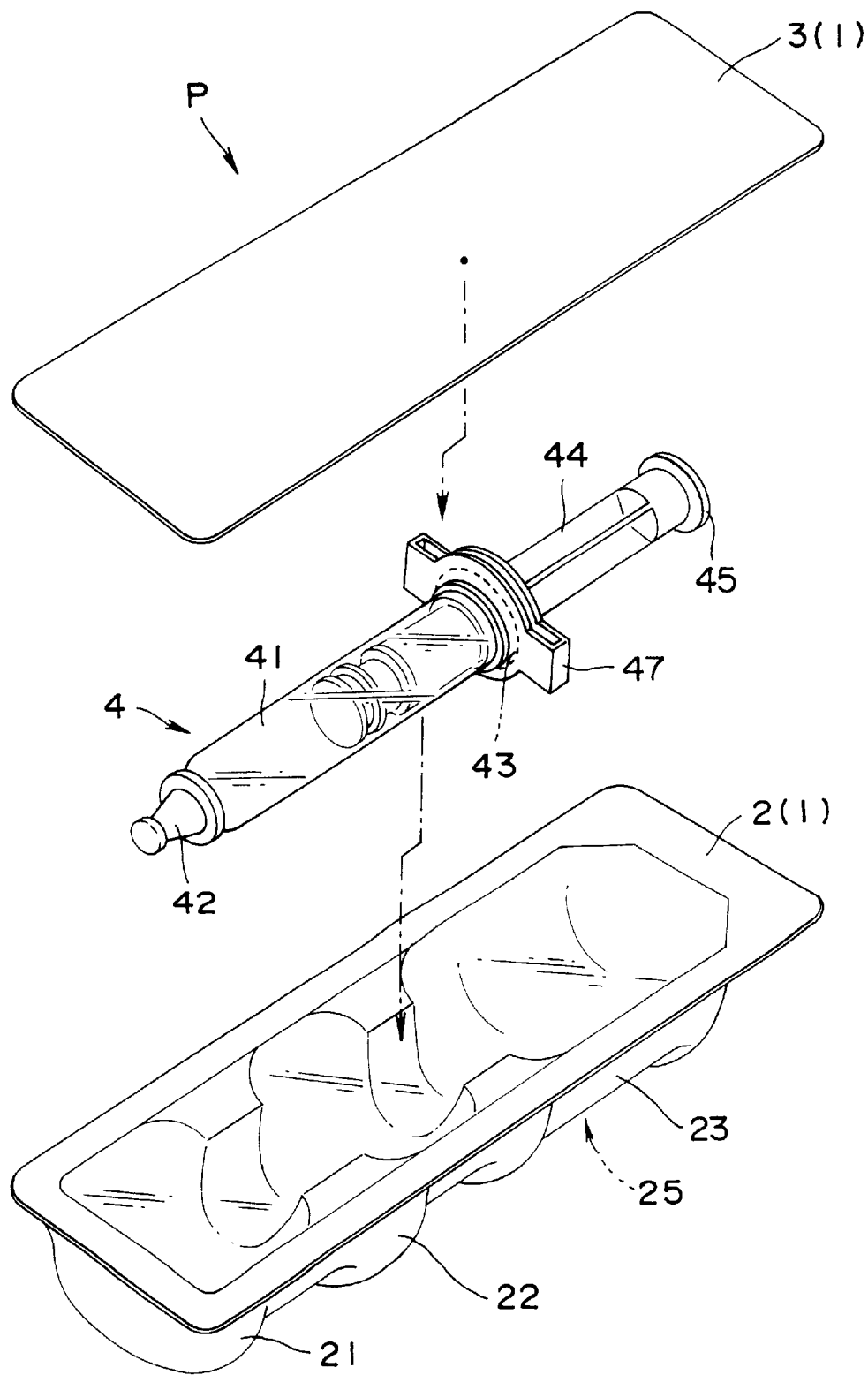
FIG. 4 is a developed perspective view showing a packaging structure of the injection pack when viewed from the bottom side.

As shown in FIG. 4, the injection pack (P) is produced by accommodating the medicine-filled injector (4) in the molded container body (2) and welding the sterile paper (3) onto the bottom surface of the container body (2) so as to enclose the medicine-filled injector (4) in the packaging container (1). As also shown in FIG. 4, onto the flange (43) of the injector cylinder (41) of the medicine-filled injector (4), there is fitted an adapter (auxiliary tool) (47) which can be hooked and pulled by the operator's fingers upon use to facilitate the injection of medicine. The adapter (47) is composed of two annular thin plates opposed to each other through a gap. Further, the adapter (47) has a function of preventing the oscillation of the medicine-filled injector (4) when the medicine-filled injector (4) is accommodated in the container body (2). Incidentally, from the standpoint of productivity, a plurality of container bodies (2) are molded in a continuous and laterally juxtaposed relation, whereby a plurality of injection packs (P) can be simultaneously produced.

Next, the chamber as a sterilizer used for carrying out the sterilizing method according to the present invention, is explained below. Such a chamber designated by reference numeral (5) in FIG. 2 may be designed, for example, as a hermetically-sealable laterally-elongated pressure container into which pallets on which packaging containers (packaged products) (1) (refer to FIG. 6) are loaded, can be charged through a door provided on one end wall thereof. To such a chamber (5) are connected a supply line (A) for a hydrogen peroxide gas, a pressure-reducing line (B), an air-introducing line (C) and a warm air-circulating line (D). Further, a catalytic reactor (54) for decomposing the hydrogen peroxide gas is disposed on the pressure-reducing line (B) and the warm air-circulating line (D).

The supply line (A) for a hydrogen peroxide gas comprises a hydrogen peroxide generator (51) composed of a mechanism for weighing and feeding a predetermined amount of a hydrogen peroxide solution and a gas-generating system for heating and gasifying the solution fed, and a conduit (71) extending from the hydrogen peroxide generator (51) through a sluice valve (61) into the chamber (5). The conduit (71) is provided at the tip end thereof with a plurality of nozzles (81) through a branched pipe.

The pressure-reducing line (B) comprises a vacuum pump (52), a conduit (72) extending from a plurality of suction ports (82) provided on the other end wall of the chamber (5), up to an intake side of the vacuum pump (52), a conduit (73) and a sluice valve (62) connected to an exhaust side of the vacuum pump (52), and the catalytic reactor (54) for converting the hydrogen peroxide gas exhausted from the chamber (5), into unharmful components. On an exhaust side of the catalytic reactor (54), a sluice valve (63) for discharging an oxygen gas resulting from the decomposition treatment is arranged. Incidentally, as the vacuum pump (52), there may be used a dry pump in order to avoid degradation of a lubricant by the hydrogen peroxide gas.

The air-introducing line (C) comprises a conduit branched from the conduit (71) and provided on an open end side thereof with a filter (64) and a sluice valve (65). More specifically, under the condition that the sluice valve (61) of the supply line (A) for hydrogen peroxide gas is closed, air can be introduced into the chamber (5) by opening the sluice valve (65).

The warm air-circulating line (D) is constituted by sequentially connecting the above catalytic reactor (54), a circulating fan (55) and a heater (56). The catalytic reactor (54) is further connected with, for example, a conduit (74) extending from a plurality of suction ports (83) provided on one side wall of the chamber (5), through a sluice valve (66). The circulating fan (55) is disposed on a rear side of the catalytic reactor (54), and the heater (56) is connected to a conduit (75) extending from an exhaust side of the circulating fan (55). The heater (56) is connected at an outlet side thereof to a conduit (76) which extends up to a plurality of blow-off ports (84) provided on the other side wall of the chamber (5). Incidentally, as described above, the catalytic reactor (54) is arranged so as to decompose the hydrogen peroxide gas flowing through both the pressure-reducing line (B) and the warm air-circulating line (D). As another example, the catalytic reactor (54) may be arranged only on the warm air-circulating line (D). As the catalytic reactor (54), there may be used known apparatuses in which a reducing agent such as platinum is accommodated.

Figure 6:
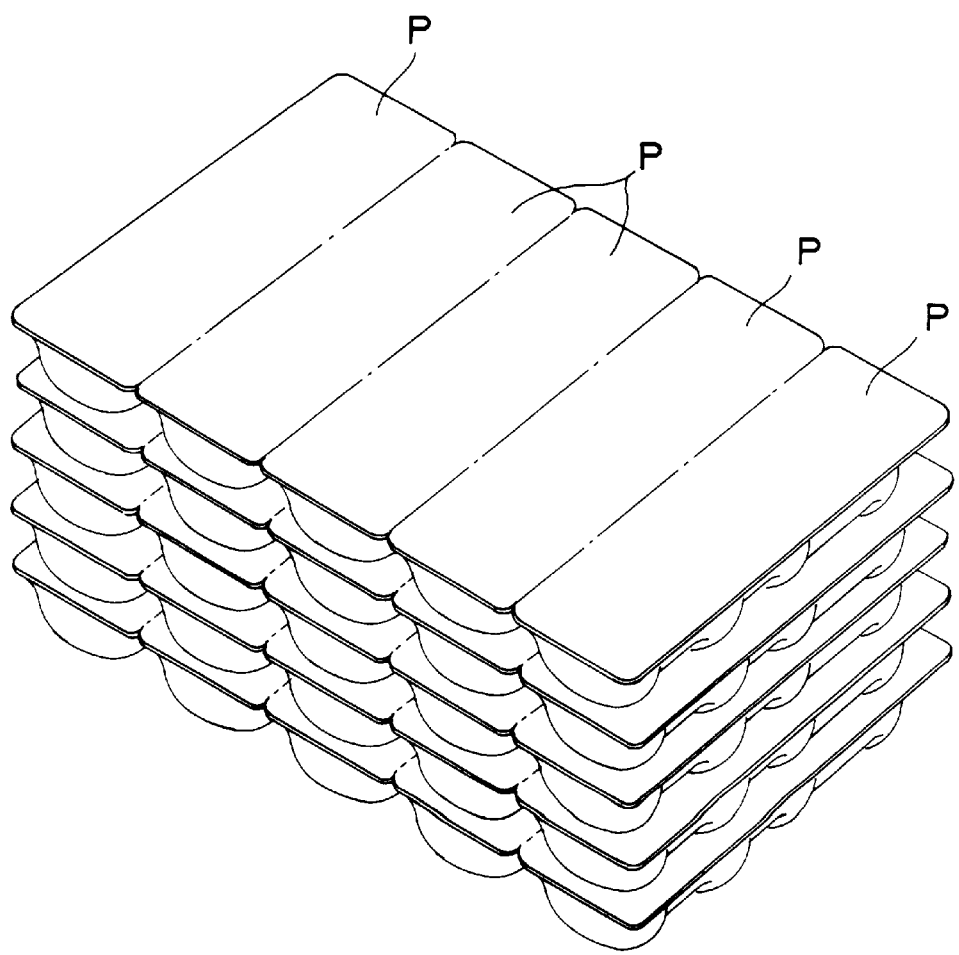
FIG. 6 is a perspective view showing the injection packs upon the sterilizing treatment.

Next, the sterilizing method using the above-mentioned chamber (5) according to the present invention, is explained below. The sterilizing method according to the present invention can be conducted by the sequential operation steps (S1) to (S9) as shown in FIG. 1. First, injection packs (P) to be sterilized are placed on a carriage, and then the carriage loaded with the injection packs are introduced into the chamber (5). At this time, as shown in FIG. 6, the injection packs (P) are loaded on the carriage in multiple rows (only one row is illustrated in the figure) and in multiple tiers or stages (step (S1)) so as to elevate the efficiency of the sterilization treatment.

After closing the chamber (5), the sluice valves (62) and (63) on the pressure-reducing line (B) are opened (the sluice valve (66) on the warm air-circulating line (D) is closed) and the vacuum pump (52) thereon is operated, so that air is discharged from an inside of the chamber through the suction ports (82), the conduits (72) and (73) and the catalytic reactor (54), thereby reducing an inner pressure of the chamber (5) to about 10 to 30 torr. Upon such a operation, in each injection pack (P) loaded, air is discharged from the inside thereof through the sterile paper (3) (step (S2)).

In the above-mentioned step (S2), in order to sufficiently penetrate the hydrogen peroxide gas into the packaging container (1), it is preferable that the degree of vacuum in the chamber (5) is adjusted to a certain high level. However, when the degree of vacuum in the chamber is too high and when air is included in the medicine-filled injector (4), there might arise such a disadvantage that the piston rod (44) is unintendedly projected out of the injector cylinder (41). Therefore, it is preferred that the degree of vacuum be set to the above-specified range.

Successively, after the operation of the vacuum pump (52) on the pressure-reducing line (B) is stopped or changed-over to idling and the sluice valves (62) and (63) are closed, the hydrogen peroxide gas is fed through the supply line (A) for hydrogen peroxide gas. The hydrogen peroxide gas is then diffused into the chamber (5) through the conduit (71) and the plural nozzles (81) by opening the sluice valve (61) and operating the hydrogen peroxide generator (51) (step (S3)).

After feeding the hydrogen peroxide gas, such a condition that the chamber (5) is filled with the hydrogen peroxide gas, is maintained for about 1 to 10 minutes, thereby sterilizing the inside of the injection pack (P) enclosing the medicine-filled injector (4). Since the inside of the injection pack (P) has been previously adjusted to a negative pressure by the pressure-reducing operation of the step (S2), it becomes possible to more effectively penetrate the hydrogen peroxide gas into the injection pack (P) through the sterile paper (3) (step (S4)).

Meanwhile, when medical products having a simple shape are sterilized, it is effective to conduct the sterilizing operation once. However, in the case where the above-mentioned injection pack (P) enclosing the medicine-filled injector is sterilized, it is required to sterilize even delicate portions such as clearances between the injector cylinder (41) and the piston rod (44) or the like. Consequently, in such a case, the above-mentioned sterilizing operation, i.e., the operation of feeding the hydrogen peroxide gas into the chamber (5) whose inner pressure is reduced, is repeated several times. Specifically, the operation including the steps (S2) to (S4) is repeated 1 to 12 times. By conducting the repeated operations, it becomes possible to ensure the penetration of the hydrogen peroxide gas into delicate portions of the medicine-filled injector (4).

After completion of repeating the sterilizing operation predetermined times, the supply line (A) for hydrogen peroxide gas is closed and the pressure-reducing line (B) is operated, thereby discharging the hydrogen peroxide gas from the chamber (5). More specifically, the sluice valve

(61) on the supply line (A) for hydrogen peroxide gas is closed, the sluice valves (62) and (63) on the pressure-reducing line (B) are opened and the vacuum pump (52) is operated, thereby discharging the hydrogen peroxide gas in the chamber. At this time, the hydrogen peroxide gas is fed to the catalytic reactor (54) where the hydrogen peroxide gas is decomposed into oxygen and water, and can be safely discharged out of the system, so that the inner pressure of the chamber (5) is reduced to about 10 to about 30 torr (step (S5)).

Next, the above-mentioned pressure-reducing line (B) is closed, and air is introduced into the chamber (5) through the air-introducing line (C). In the air-introducing operation, by opening the sluice valve (65), air is introduced through the filter (64), the conduit (71) and the plural nozzles (81), thereby restoring the inner pressure of the chamber (5) to an atmospheric pressure. After the inner pressure of the chamber reaches an atmospheric pressure, the sluice valve (65) is closed (step (S6)).

Successively, the hydrogen peroxide gas remaining in the injection pack (P) is removed. Although the hydrogen peroxide gas can be removed to some extent only by exposing to air, there arises a problem that it is required to allow the injection pack to stand in air for an extremely long period of time. Further, there arises another problem that when the container body of the packaging container is composed of some kinds of materials, e.g., the polyester-based resins such as PET, the hydrogen peroxide gas cannot be completely removed due to a high adsorptivity of the hydrogen peroxide gas. For this reason, in the present invention, the injection pack (P) is subjected to the degassing treatment while heating in order to remove the hydrogen peroxide gas therefrom. As a result, it becomes possible to accelerate the desorption of the hydrogen peroxide gas from the container body (2), more readily remove the hydrogen peroxide gas and surely prevent the hydrogen peroxide gas from remaining in the injection pack. As the preferred heating method, there may be used a method of circulating heated air to the chamber (5).

More specifically, the sluice valve (66) on the warm air-circulating line (D) is opened, and the circulating fan (55) and the heater (56) are operated. The circulating fan (55) operates to inhale air in the chamber (5) drawn from the plural suction ports (83), in the catalytic reactor (54) through the conduit (74). The air from which the hydrogen peroxide gas is removed in the catalytic reactor (54) is fed to the heater (56) through the conduit (75). The air heated by the heater (56) is returned to the chamber (5) through the plural blow-off outlets (84) (step (S7)).

In addition, in the above-mentioned step (S7), it is important to set the inside of the chamber (5) to an appropriate temperature, i.e., to conduct the degassing treatment for removing the hydrogen peroxide gas from the inside of the injection pack (P) under such a condition that the temperature of warm air supplied is adjusted to about 30 to about 120° C., preferably 30 to 100° C. by controlling the heater (56). The reason for defining the temperature condition is as follows. That is, when the temperature of the warm air is less than 30° C., it may be difficult to desorb the hydrogen peroxide gas from the surface of the polyester-based resin film from which the container body (2) is formed, resulting in deteriorated degassing efficiency. On the other hand, when the temperature of the warm air is more than 120° C., there is a tendency that the medicine filled in the medicine-filled injector (4) is heated to substantially 100° C. or higher, thereby causing the degradation thereof.

The degassing treatment of the step (S7) may be usually conducted for about 30 to about 120 minutes, so that the hydrogen peroxide gas remaining in the injection pack (P) is caused to penetrate through the sterile paper (3), discharged therefrom and decomposed in the catalytic reactor (54) disposed in the warm air-circulating line (D). More specifically, while circulating the heated air to the chamber (5), the hydrogen peroxide gas contained in the circulated air is subjected to catalytic reaction for decomposition thereof, thereby maintaining the concentration of the hydrogen peroxide gas in the chamber (5) at a low level, and thus effectively and safely conducting the degassing treatment for removal of the hydrogen peroxide gas. After completion of the degassing treatment for removal of the hydrogen peroxide gas, the circulating operation of the warm air-circulating line (D) is stopped and the injection pack (P) treated is removed from the chamber (5) (step (S8)).

Incidentally, after the degassing treatment, i.e., after completing the operation of the step (S7), atmospheric air may be temporarily introduced into the chamber (5). By feeding fresh air into the chamber (5), the temperature in the chamber (5) and in the injection pack (P) can be decreased, so that it becomes possible to immediately initiate handling of subsequent treatments. Besides, even if a trace amount of the hydrogen peroxide gas remains in the injection pack due to malfunction of the catalytic reactor (54), etc., the safe operation is ensured by replacing air in the chamber with fresh one.

As described above, in the sterilizing method according to the present invention, since the packaging container (1) comprising the container body (2) composed of the specified material and having the specified shape, and the sterile paper (3), is used as a container, even when the injection packs are stacked up in multiple stages and exposed to the gas, the contact area between the upper-stage and lower-stage injection packs (P) is lessened, thereby enhancing an efficiency of contact between the sterile paper (3) of the packaging container (1) and the hydrogen peroxide gas and air, and therefore, rapidly conducting the sterilizing treatment and the degassing treatment.

More specifically, in the above-mentioned injection packs (P), since the constricted portions of the container body (2) form clearances between the upper-stage and lower-stage packaging containers (1), the hydrogen peroxide gas can be distributed over a whole part of the stacked-up injection packs (P). The largest third swelled portion (23) of the container body (2) accommodating the flange (43) of the injector cylinder (41) of the medicine-filled injector (4) and the pusher (45) of the piston rod (44) is formed into a saddle shape recessed at a central portion thereof, so that the contact area between the upper-stage and lower-stage packaging containers (1) is small, thereby enhancing an efficiency of contact between the sterile paper (3) of the packaging container (1) and the hydrogen peroxide gas.

In addition, after completion of the sterilizing treatment, by discharging the hydrogen peroxide gas in the chamber and exposing the injection pack (P) to air introduced, the interior of the packaging container (1) is degassed to remove the hydrogen peroxide gas therefrom. At this time, in a similar manner to the sterilizing treatment, the constricted portions (24) of the container body (2) enables air to be distributed over a whole part of the stacked-up injection packs (P), and the third swelled portion (23) can enhance an efficiency of contact between the sterile paper (3) and air.

More specifically, in the injection pack (P) according to the present invention, since the container body (2) of the packaging container (1) is formed into the above-specified shape, and therefore, a sufficient gas-penetrating area of the sterile paper (3) is ensured even when the injection packs are stacked up in multiple stages, it is possible to penetrate the hydrogen peroxide gas into the packaging container (1) for a short period of time in the sterilizing treatment, and degas the interior of the packaging container (1) for a short period of time to remove the hydrogen peroxide gas therefrom. Therefore, the injection pack (P) according to the present invention can be further improved in efficiency of sterilizing treatment thereof.

Further, in the sterilizing treatment of the present invention, after completion of the sterilizing treatment by hydrogen peroxide gas, the injection pack (P) is degassed while introducing the warm air having a predetermined temperature thereinto in order to remove the hydrogen peroxide gas from an inside thereof, thereby accelerating the desorption of the hydrogen peroxide gas from the container body (2). Therefore, the degassing treatment can be conducted efficiently and the hydrogen peroxide gas can be surely prevented from remaining in the injection pack. Besides, in the degassing treatment for removal of the hydrogen peroxide gas, while circulating heated air, the hydrogen peroxide gas contained in the circulated air is decomposed by catalytic reaction thereof. As a result, since the concentration of the hydrogen peroxide gas in the chamber (5) can be always maintained at a lower level than that in the injection pack (P) and the difference in concentration of the hydrogen peroxide gas therebetween allows the gas to penetrate through the sterile paper (3), it is possible to degas the injection pack (P) more efficiently to remove the hydrogen peroxide gas from the inside thereof. Accordingly, as the container body (2), there can also be used a container body composed of a polyester-based resin which exhibits an excellent transparency and is easy to conduct the disposal treatment.

Figure 2:
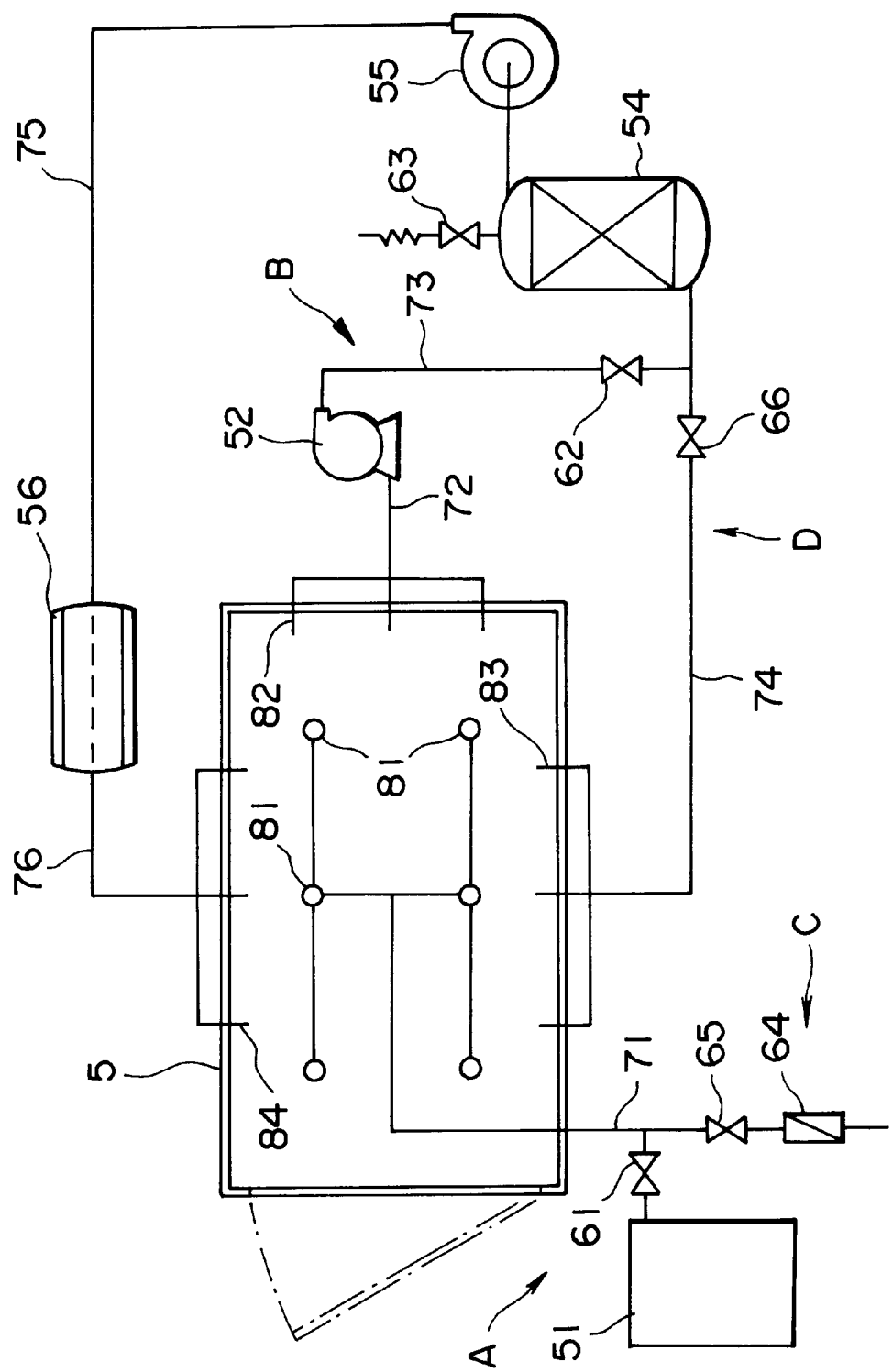
FIG. 2 is an outlined system diagram showing a chamber as a sterilizing equipment for carrying out the sterilizing method according to the present invention.

Incidentally, the injection pack (P) was constituted from the container body (2) composed of a PET film and the sterile paper (3) composed of the above-mentioned "TYVEK", and the injector filled with sodium hyaluronate as medicine was enclosed in the injection pack (P). The thus-constituted injection packs were divided into two treating lots (a) and (b) each of which was then subjected to sterilizing treatment with hydrogen peroxide gas, using the chamber (5) as shown in FIG. 2. In that case, the lot (a) was sterilized by the sterilizing method according to the present invention. On the other hand, for a comparative purpose, the lot (b) was subjected to the steps (S1) to (S6) as shown in FIG. 1, and then allowed to stand at an ordinary temperature in atmospheric air, thereby subjecting the lot (b) to degassing treatment. As a result, it was determined that the hydrogen peroxide gas was completely removed from the injection packs (P) of the lot (a) by subjecting to the degassing treatment (step (S7)) for 2 hours, while the injection pack (P) of the lot (b) still contained residual hydrogen peroxide gas in an amount of about 100 ppm even after subjecting to the above degassing treatment for 6 hours.

In the sterilizing method according to the present invention, especially the degassing treatment in which the hydrogen peroxide gas is removed from the injection pack (P) by the circulation of the warm air, can exhibit remarkable effects from industrial and environmental standpoints. Specifically, in the above degassing operation, the amount of air discharged out of the system which has been used for the degassing treatment, and may contain the hydrogen peroxide gas even in a trace amount, can be reduced to a large extent, and the heat load required to produce the warm air can also be reduced to a large extent. In order to accelerate the degassing effect, it is preferable to reduce the concentration of hydrogen peroxide gas in air returned to the chamber as low as possible. In accordance with the present invention, by using the catalyst and elevating a temperature of the circulated air, the hydrogen peroxide gas in the circulated air can be surely and safely treated. Besides, since the hydrogen peroxide gas which can be catalytically decomposed into unharmful components, is used as a sterilizing gas, extremely high safety can be assured not only upon the sterilizing treatment but also when the exhaust gas is finally discharged out of the system.

In the sterilizing method according to the present invention, the desorption of the hydrogen peroxide gas adsorbed in the container body can be accelerated and the hydrogen peroxide gas can be surely prevented from remaining in the container. Therefore, the sterilizing method can be suitably applied to medical sterilization packaging for medical products such as injection packs, etc., in which the surfaces of the medical products and the inside of the packaging container are sterilized by the hydrogen peroxide gas while keeping packaged. In addition, the injection pack according to the present invention can allow the sterilizing gas to penetrate into the packaging container for a short period of time in the sterilizing treatment, and the sterilizing gas can be removed from the inside of the packaging container for a short period of time, thereby further enhancing an efficiency of the sterilizing treatment. Accordingly, the present invention is suitable for more efficient production of injection packs an inside of which is sterilized. Further, in another preferred embodiment of the present invention, there is provided an injection pack having such a structure that an injector previously filled with sodium hyaluronate is enclosed in a packaging container composed of PET, and the packaging container is sealed by a sterile paper. The injection pack is a sterilized package product an inside of which is sterilized by the hydrogen peroxide gas while keeping the sealed condition, and which can maintain the sterilized condition up to the use thereof.

What is claimed is:

1. A method of sterilizing a medical product enclosed in a packaging container by a hydrogen peroxide gas, comprising:

using as said packaging container, a container comprising a container body composed of a synthetic resin having a gas-barrier property, and a sterile paper capable of allowing said hydrogen peroxide gas to penetrate therethrough and weldable to said container body; and after the sterilization by said hydrogen peroxide gas, subjecting said packaging container enclosing said medical product to degassing treatment at a temperature of between about 30 to about 120° C., thereby removing said hydrogen peroxide gas from an inside of said packaging container.

2. A sterilizing method according to claim 1, which further comprises:

placing said medical product enclosed in said packaging container in a chamber as a sterilizer to subject said medical product enclosed in said packaging container to sterilizing treatment; and while circulating heated air to said chamber, decomposing said hydrogen peroxide gas contained in said circulated heated air by catalytic reaction, thereby conducting degassing treatment for removal of said hydrogen peroxide gas.

3. A sterilizing method according to claim 2, wherein after completion of the degassing treatment, atmospheric air is introduced into said chamber.

4. A sterilizing method according to claim 2, wherein the sterilizing treatment is conducted by repeating an operation of feeding said hydrogen peroxide gas into said chamber whose inside pressure is reduced, 1 to 12 times.

5. A sterilizing method according to claim 2, wherein a chamber to which a supply line for hydrogen peroxide gas, a pressure-reducing line, an air-introducing line and a warm air-circulating line are connected, is used as said chamber, and a catalyst apparatus for decomposing said hydrogen peroxide gas is arranged on said warm air-circulating line.

6. A sterilizing method according to claim 1, wherein said medical product is a medicine-filled injector.

7. A sterilizing method according to claim 6, wherein the medicine filled in said medicine-filled injector is a sodium hyaluronate solution.

8. A sterilizing method according to claim 6, wherein said packaging container comprises:
- a container body which is composed of a transparent resin, integrally molded into an approximate elongated vessel shape and opened at bottom thereof, and
- a sterile paper composed of a sheet material capable of allowing said hydrogen peroxide gas to penetrate therethrough and closing the open bottom of said container body,
- said container body comprising a first swelled portion for receiving a needle-fitting portion of an injector cylinder of said medicine-filled injector,
- a second swelled portion for receiving an approximately central portion of said medicine-filled injector,
- a third swelled portion for receiving a flange of said injector cylinder and a pusher of a piston rod, and
- two constricted portions connecting said swelled portions to each other,
- said third swelled portion being formed into a saddle shape recessed at a central portion thereof when viewed from the longitudinal side of said container body.

9. A sterilizing method according to claim 8, wherein the height of said second swelled portion is lower than those of said first and third swelled portions.

10. A sterilizing method according to claim 8, wherein said container body comprises a polyester-based resin.

11. An injection pack comprising a packaging container and a medicine-filled injector enclosed in said packaging container,
- said packaging container comprising a container body which is composed of a transparent resin, integrally molded into an approximate elongated vessel shape and opened at bottom thereof, and
- a sterile paper composed of a sheet material capable of allowing a sterilizing gas to penetrate therethrough and closing the open bottom of said container body,
- said container body comprising a first swelled portion for receiving a needle-fitting portion of an injector cylinder of said medicine-filled injector,
- a second swelled portion for receiving an approximately central portion of said medicine-filled injector,
- a third swelled portion for receiving a flange of said injector cylinder and a pusher of a piston rod, and
- two constricted portions connecting said swelled portions to each other,
- said third swelled portion being formed into a saddle shape recessed at a central portion thereof when viewed from the longitudinal side of said container body.

12. An injection pack according to claim 11, wherein the height of said second swelled portion is lower than those of said first and third swelled portions.

13. An injection pack according to claim 11, wherein said container body comprises a polyester-based resin.

14. An injection pack according to claim 11, wherein the inside of said packaging container is sterilized by a hydrogen peroxide gas while enclosing said medicine-filled injector and keeping the open bottom of said container body closed by said sterile paper.

15. An injection pack according to claim 11, wherein the medicine filled in said medicine-filled injector is a sodium hyaluronate solution.

* * * * *